United States Patent [19]

Downing

[11] 4,159,596

[45] Jul. 3, 1979

[54] MEANS AND A METHOD FOR THE SELF-POLLINATION OF CORN

[76] Inventor: Gilbert Downing, 2380 Harrison Rd., New Madison, Ohio 45346

[21] Appl. No.: 874,837

[22] Filed: Feb. 3, 1978

[51] Int. Cl.² .......................... A01G 7/00; A01H 1/02
[52] U.S. Cl. ........................................ 47/58; 47/1.41; 47/26
[58] Field of Search .................... 47/1.41, 20–21, 47/26, 28–29, 41, 58; 206/423

[56] References Cited

U.S. PATENT DOCUMENTS

| 1,446,416 | 2/1923 | Curtiss | 47/21 |
|---|---|---|---|
| 2,056,514 | 10/1936 | Garcia | 47/26 |
| 2,446,509 | 8/1948 | Fischer | 47/1.41 X |
| 3,987,583 | 10/1976 | Takeyasu | 47/29 |

FOREIGN PATENT DOCUMENTS

| 3487 | 11/1900 | Austria | 47/26 |
|---|---|---|---|
| 250053 | 7/1911 | Fed. Rep. of Germany | 47/28 |
| 497001 | 6/1976 | U.S.S.R. | 47/1.41 |

OTHER PUBLICATIONS

Life, Oct. 31, 1955, vol. 39, No. 18, p. 112 cited.
Seeds, Yearbook of Agriculture 1961, U.S.D.A., p. 129 cited.

*Primary Examiner*—Robert E. Bagwill
*Attorney, Agent, or Firm*—Melville, Strasser, Foster & Hoffman

[57] ABSTRACT

A means and method for the self-pollination of corn wherein a single bag structure is utilized. The bag comprises an elongated tubular member. The upper end of the bag is configured such that it may be located and closed about a corn plant tassel. The lower end of the bag is adapted to receive an ear shoot of the corn plant. The bag is mounted on the corn plant before any ear shoot silk is exposed and remains in place until harvest. The bag concentrates the pollen from the corn plant tassel on the earliest to the latest ear shoot silk to produce a well filled ear of high inbred purity and yield.

11 Claims, 10 Drawing Figures

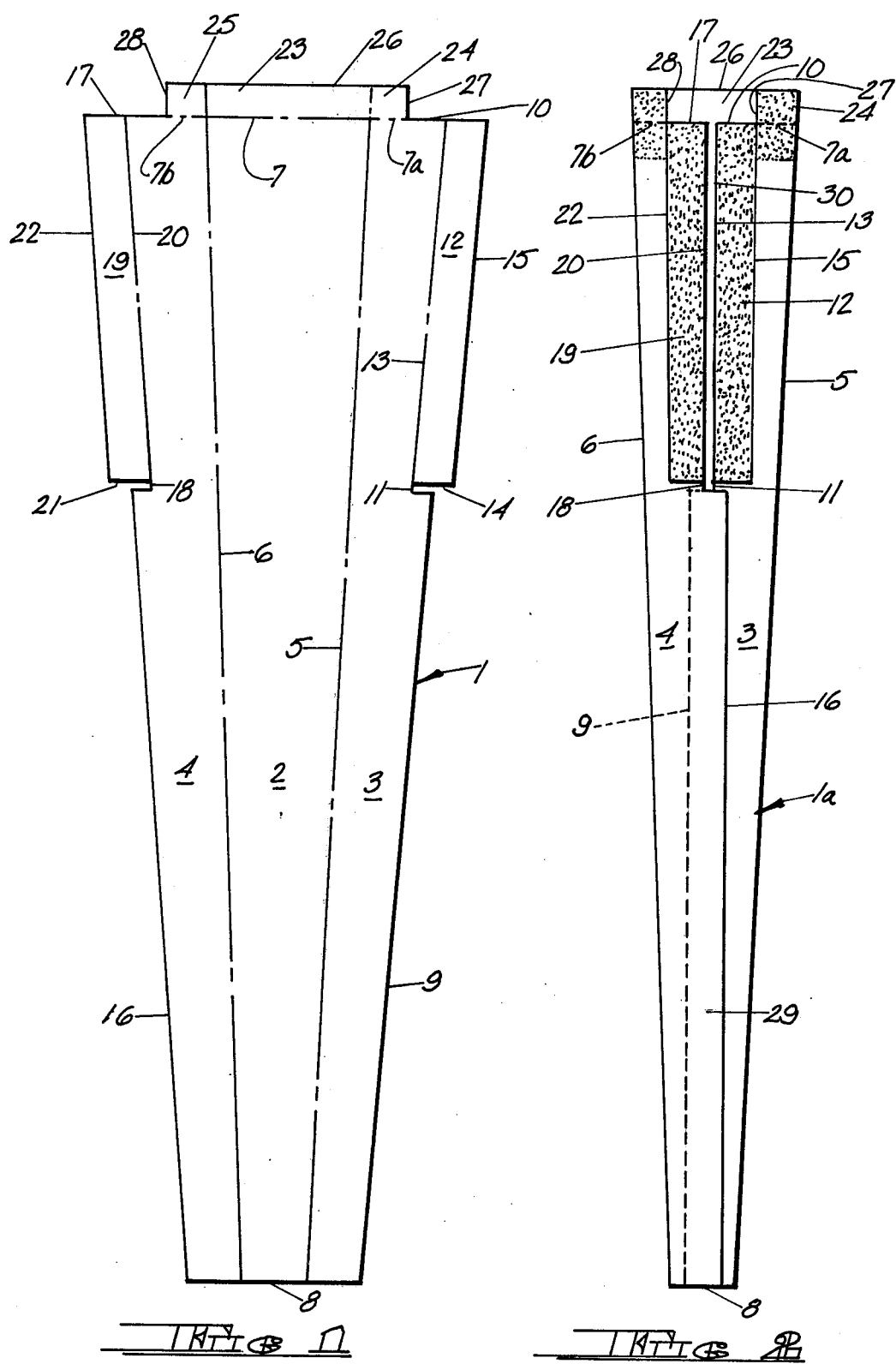

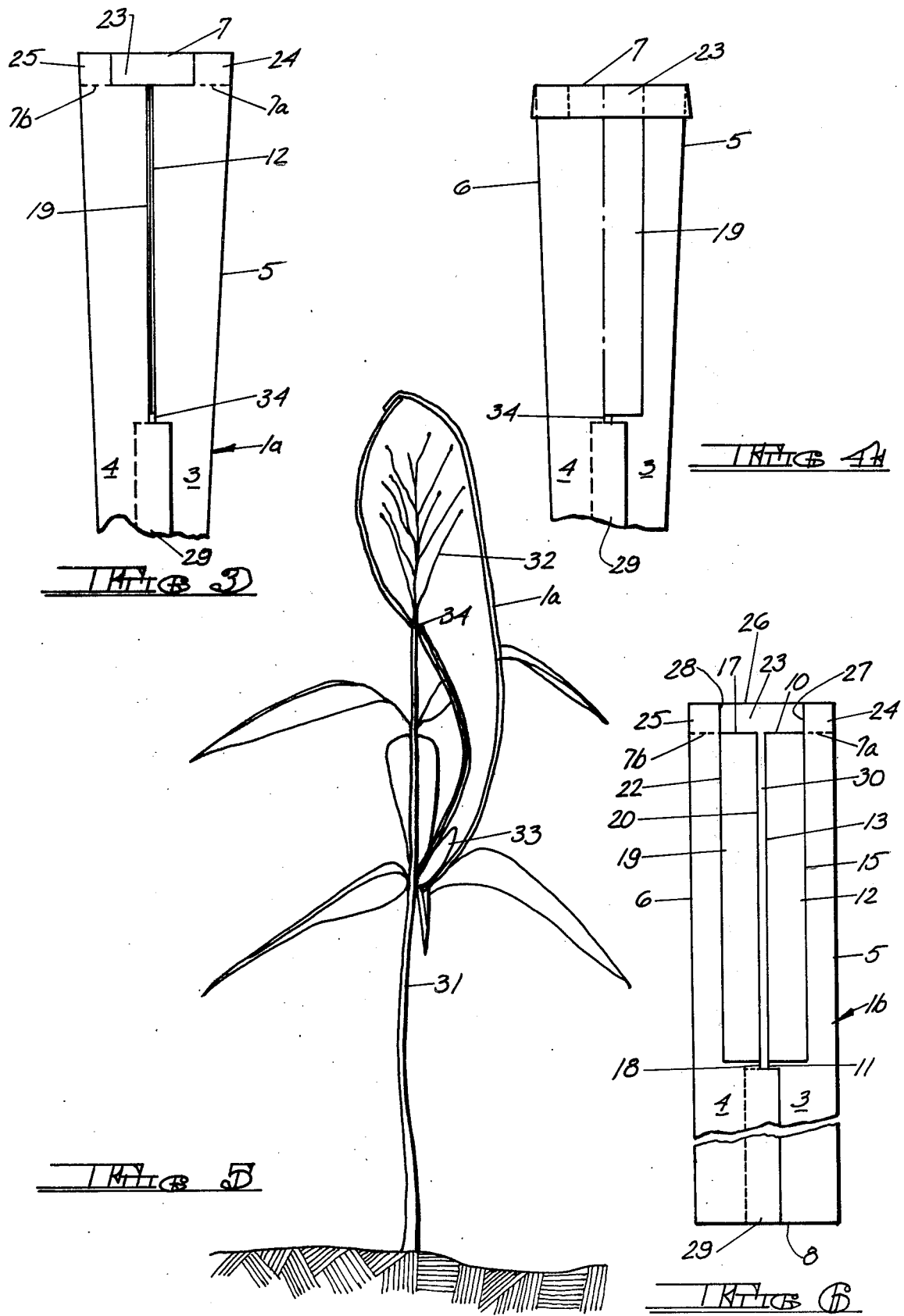

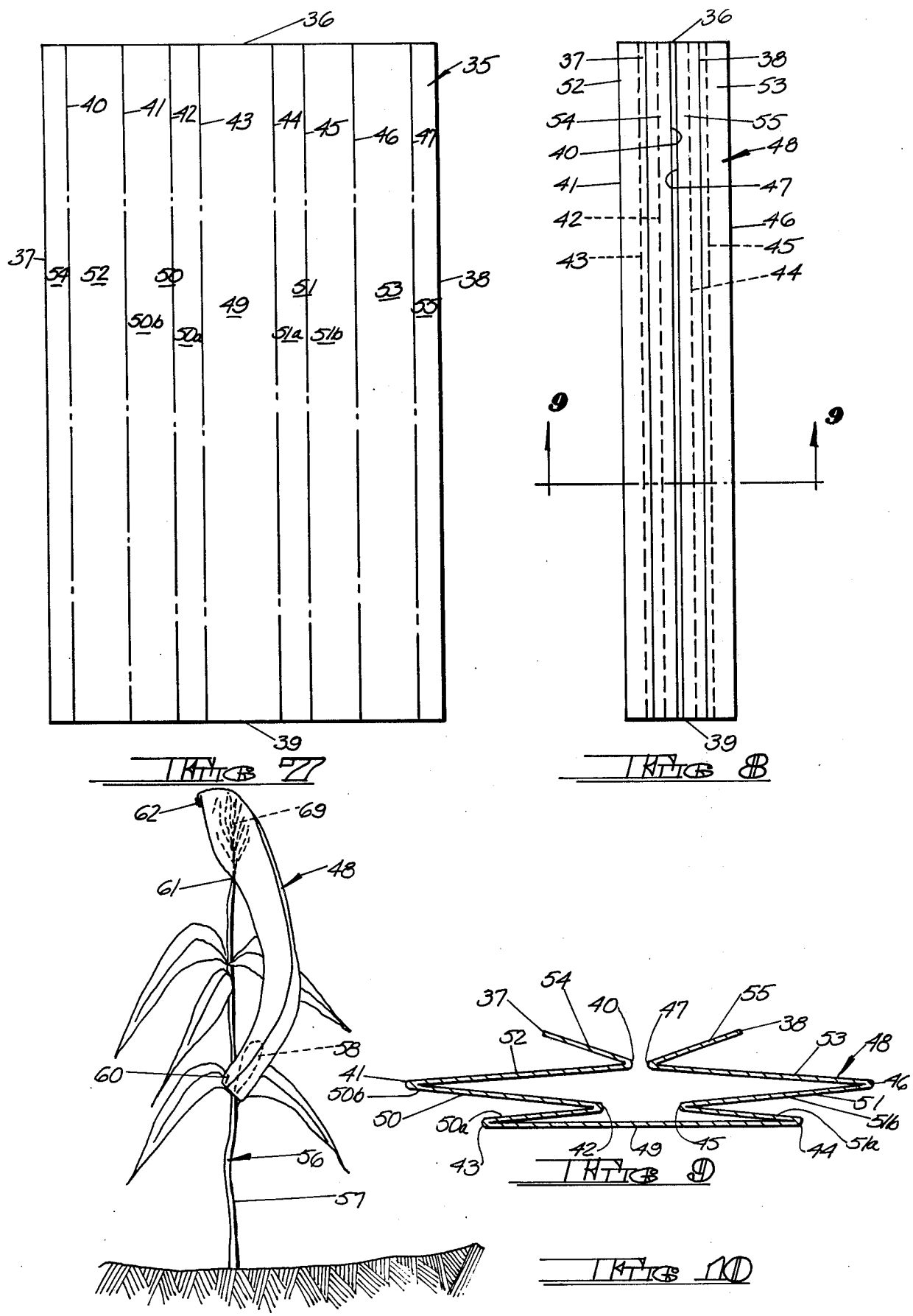

MEANS AND A METHOD FOR THE SELF-POLLINATION OF CORN

BACKGROUND OF THE INVENTION

1. Field of the Invention

The invention relates to a means and method for the self-pollination of corn and more particularly to a single bag method utilizing an elongated tubular bag adapted to accommodate both the tassel and an ear shoot of a corn plant.

2. Description of the Prior Art

In the usual procedure for the self-pollination of corn a two bag system is utilized. Before any of the ear shoot silk is exposed, it is the usual procedure to provide each corn plant with a first bag placed and tied about the corn plant tassel and a second bag placed and tied about the corn plant ear shoot. At an appropriate time in the growing cycle, the first bag in which pollen from the tassel has collected is used to replace the second bag about the ear shoot. Alternatively, the second bag about the ear shoot is torn open and pollen from the first bag is poured thereinto, the first bag thereafter being placed about both the ear shoot and the second bag and tied in place.

In accordance with the present invention, a single bag is applied to each corn plant prior to the exposure of any ear shoot silk. The single bag is of elongated tubular configuration and is adapted at its upper end to be placed and closed about the corn plant tassel. The lower end of the bag is adapted to receive the ear shoot. All of the pollen produced by the corn plant is funneled down the tubular bag and onto the silk of the ear shoot. Since the bag is placed on the plant before the ear shoot silk is exposed and is left there until harvest, there is no chance of stray pollen reaching the ear shoot silk.

The means and method of the present invention saves time, labor and expense in the corn growing operation since it requires only one application of only one bag per plant and eliminates several steps of the growing operation. All of the pollen produced by a corn plant is funneled to the silk of that plant's ear shoot, concentrating the pollen on the silk and eliminating the chance of stray pollin reaching the silk. The process is a continuing one so that the earliest to the latest silk are all pollinated. As a consequence, the means and method of the present invention produces a well filled ear, increasing yield and resulting in the ultimate in inbred purity. Furthermore, pollen may be easily collected at the lower end of the tubular bag, without removing the bag from the plant, when there is a need of pollen for crossing on another corn plant.

SUMMARY OF THE INVENTION

The means and method for the self-pollination of corn contemplates the use of a single bag structure. In one embodiment, the bag is of elongated tubular configuration, tapering slightly from its upper end to its lower end. The upper end of the bag is open and is provided with a longitudinal slot terminating in a tassel stem receiving opening. The slot itself is flanked with a pair of closure flaps and the upper end of the bag is provided with additional closure flaps. As a consequence, the upper end of the bag may be located about a corn plant tassel with the lower end of the tassel stem extending outwardly of the bag through the stem opening therein. When the upper end of the bag is placed about the tassel, the closure flaps flanking the slot are joined together by appropriate means. The additional flaps at the upper end of the bag are folded to closed position and are maintained in closed position by appropriate means. As a result, the corn plant tassel is completely enclosed in the upper end of the bag.

The lower end of the bag is open and is adapted to be placed over the ear shoot of the corn plant. If desired, means may be provided to gather and close the lower end of the bag about the base of the ear shoot. These means may be separate means or means affixed to or otherwise associated with the lower end of the bag.

A second embodiment of the bag of the present invention is substantially identical to the first embodiment, differing only in that it is not longitudinally tapered. In a third embodiment, the bag of the present invention comprises a front panel, a narrower back panel and pleated side panels. The front panel is made up of two halves, the longitudinal free edges of which are provided with cooperating closure flaps extending the full length of the bag. The closure flaps may be joined together at the lower end of the bag and the lower end of the bag can be placed over the ear shoot of a corn plant. The lower end of the bag is then wrapped about the corn plant stalk and fastened together on the opposite side of the stalk from the ear shoot, thus securing the lower end of the bag to the stalk and about the ear shoot.

The closure flaps may thereafter be joined together up to and about the base of the corn plant tassel, and then all the way to the upper end of the bag, enclosing the tassel. The uppermost end of the bag is then folded down and fastened shut.

Thus, when any one of the above mentioned bags is mounted on a corn plant, its upper end completely encloses the corn plant tassel and its lower end completely encloses the corn plant ear shoot, the remainder of the bag serving as a conduit between the tassel and the ear shoot.

In accordance with the method of the present invention, any one of the bags mentioned above is mounted on the corn plant (as described) before any silk of the ear shoot is exposed. The bag is left in position on the plant until harvest so that the pollen from the tassel is concentrated on the silk of the ear shoot with the earliest to the latest silk being pollinated to produce a well filled ear. The means and method provide excellent inbred purity and yield.

It is also within the scope of the invention to collect pollen at the lower end of the bag, without removing the bag from the corn plant, when pollen is needed for crossing on another corn plant. If desired, any one of the above mentioned bags could be used to interconnect the tassel of one corn plant and the ear shoot of an adjacent corn plant.

BRIEF DESCRIPTION OF THE DRAWINGS

FIG. 1 is an elevational view of the blank from which the first embodiment of the bag of the present invention is formed.

FIG. 2 is an elevational view of the fully formed bag ready for use.

FIG. 3 is a fragmentary elevational view of the upper end of the bag illustrating the flaps flanking the slot in their closed condition.

FIG. 4 is a fragmentary elevational view of the upper end of the bag, similar to FIG. 3, and illustrating the upper end closure flaps in folded and closed position.

FIG. 5 is a cross sectional view of the bag of FIGS. 1 through 4 shown mounted on a corn plant.

FIG. 6 is a fragmentary elevational view of a second embodiment of the bag of the present invention, differing from that of FIG. 2 primarily in that the bag is not longitudinally tapered.

FIG. 7 is an elevational view of the blank from which is form the third embodiment of the bag of the present invention.

FIG. 8 is an elevational view of fully formed bag of FIG. 7 ready for use.

FIG. 9 is a cross sectional view taken along section line 9—9 of FIG. 8.

FIG. 10 illustrates the bag of FIGS. 7 through 9 as applied to a corn plant.

DESCRIPTION OF THE PREFERRED EMBODIMENTS

The blank of FIG. 1 is preferably an integral one-piece structure and comprises what, for purposes of convenience, will be termed a back panel 2 and a pair of front panels 3 and 4. The back panel 2 is defined by a pair of longitudinal fold lines 5 and 6, a fold line 7 near the upper end of the blank and the lower edge 8 of the blank. Front panel 3 is defined by longitudinal fold line 5, the longitudinal blank edge 9, the lower edge 8 of the blank and an upper edge 10 of the blank together with a continuation of fold line 7, as shown at 7a. Front panel 3 is notched as at 11 and has near the upper end of the bag a flap portion 12. The flap portion 12 is defined by a fold line 13 between it and the front panel 3, a lower edge 14 adjacent notch 11, a free longitudinal edge 15 and the top edge portion 10 of the blank.

In similar fashion, the front panel 4 is defined by longitudinal fold line 6, longitudinal free edge 16, the lower edge 8 of the blank and an upper edge portion 17 of the blank together with a continuation of fold line 7, as shown as 7b. The upper edge portion 17 of the blank corresponds to the upper edge portion 10. The front panel 4 has a notch 18 formed therein, corresponding to the notch 11 of front panel 3. Front panel 4 also has an integral flap portion 19, corresponding to flap portion 12 of front panel 3. The flap 19 is defined by the longitudinal fold line 20 between it and front panel 4, the lower edge 21 defined by notch 18, the longitudinal free edge 22 and the upper edge portion 17 of the blank.

From the above description, it will be evident that front panel 3 and front panel 4 are essentially mirror images of each other, located to either side of rear panel 2.

At the upper end of the blank 1 there are three additional flaps 23, 24 and 25. The flap 23 is in essence a continuation of back panel 2 and is defined by fold line 7, fold lines 5 and 6 and the uppermost edge portion 26 of the blank. The flap 24 is a continuation of flap 23 and is defined by fold line 5, fold line 7a, upper edge portion 26 and vertical edge portion 27. In similar fashion, the flap 25 is a continuation of flap 23 and is defined by fold lines 6 and 7b, edge portion 26 and vertical edge portion 28.

FIG. 2 illustrates the blank 1 as formed into the bag of the present invention, ready for use. In FIG. 2 like parts have been given like index numerals.

The formation of blank 1 into the bag of the present invention is accomplished by folding the blank along fold lines 5 and 6 so that front panels 3 and 4 overlie rear panel 2. The flap portion 12 of front panel 3 is folded along fold line 13 so as to overlie front panel 3. In similar fashion, the flap portion 19 of front panel 4 is folded so as to overlie front panel 4.

When the blank is so folded, the fold lines 5 and 6 will form the longitudinal edges of the bag. As will be evident from FIG. 2, front panels 3 and 4 are so sized that their longitudinal edges 9 and 16 overlap each other. For purposes of an exemplary showing, front panel 4 is illustrated as overlying a portion of front panel 3. The front panel 3, it will be understood, could just as easily overlie front panel 4. The overlapped portions of front panels 3 and 4 (defined between longitudinal edges 9 and 16) form a lapped seam 29 which may be secured together in any appropriate way, as by adhesive or the like.

When the flaps 12 and 19 are folded oppositely so as to overlie front panel 3 and front panel 4, respectively, the fold lines 13 and 19 define the edges of a longitudinal slot 30 extending from the upper end of the bag to the upper end of lapped seam 29. It is important to note that longitudinal slot 30 is of a slightly greater length than flaps 12 and 19. The reason for this will be explained hereinafter. Finally, it will be noted that flaps 24 and 25 at the upper end of the bag overlap in part the flap 23. Both the upper end and the lower end of the bag are open.

The bag may be made of any suitable, flexible material capable of withstanding the elements including sun, wind, rain and the like. Exemplary, but non-limiting, materials from which the bag may be made comprise wet strength paper or vegetable parchment. The material of the bag must be of such nature that it will not permit escape of pollen from within or the entrance of stray pollen from without. When the lapped seam 29 is formed with the use of an adhesive, the adhesive must be characterized by sufficient strength and water proof qualities to withstand the elements.

FIG. 5 illustrates the bag 1a mounted on a corn plant 31. The upper end of bag 1a is adapted to receive and enclose the corn plant tassel 32, while the lower end of the bag 1a is adapted to receive and encompass the corn plant shoot 33.

It will be evident from FIG. 5 that the stem or base of the corn plant tassel passes through an opening 34 in the bag 1a. The opening 34 comprises that endmost portion of slot 30 in the bag which extends beyond the flaps 12 and 19. This will be more evident from a consideration of FIGS. 3 and 4 which demonstrate the manner in which the upper end of the bag 1a is closed. The corn plant is not shown in FIGS. 3 and 4 for purposes of clarity.

The tassel 32 of the corn plant is enclosed in the upper end of bag 1a by pulling the flaps 12 and 19 at the upper end of the bag away from each other to cause the slot 30 to open up into a sort of V-shaped opening. The upper end of the bag is brought about the corn plant tassel 32 with the stem or base portion of the tassel located at the lowermost end of slot 30. The opposed faces of flaps 12 and 19 are then abutted and appropriately joined together to close the slot 30. Flaps 12 and 19 are illustrated in such position in FIG. 3. With the flaps 12 and 19 joined together, the opening 34 in the bag for the stem is clearly shown in FIG. 3. While the opposed faces of flaps 12 and 19 may be joined together by any appropriate means, a preferred but non-limiting way of accomplishing this is to precoat the opposed faces of these flaps with any appropriate water proof contact or pressure sensitive adhesive so that the flaps may be jointed together by simply pressing their opposed faces together. A coating of adhesive on flaps 12 and 19 is indicated in FIG. 2 by stippling.

The uppermost end of the bag 1a is thereafter closed by folding flaps 12 and 19 against either front panel 4 or front panel 3 (as shown in FIG. 4) and thereafter folding flaps 23, 24 and 25 downwardly against front panels 3 and 4 as shown in FIG. 4. When this is done, fold line 7 becomes the uppermost edge of the bag, as is evident from FIG. 4.

Flaps 23, 24 and 25 may be held in the folded position illustrated in FIG. 4 by any appropriate means. Again, a non-limiting manner in which this may be accomplished would be to coat the flaps 24 and 25 and the adjacent portions of front panels 3 and 4 with a water proof, pressure sensitive or contact adhesive so that when the flaps are in their folded position, flaps 24 and 25 will be adhered to the adjacent portion of front panels 3 and 4 by simply pressing them thereagainst. Such an adhesive coating on the flaps 24 and 25 and the adjacent portions of front panels 3 and 4 is again indicated by stipling in FIG. 2. It would be within the scope of the invention to provide additional adhesive coating to the central portion of the inside surface of flap 23 and an adjacent portion of flap 19.

The lowermost end of bag 1a may simply be placed over ear shoot 33. Since the bag 1a, as thus far illustrated, is longitudinally tapered so as to have a small internal diameter at its bottom end, it will tend to stay in place on the ear shoot. It is within the scope of the invention, however, to gather the lowermost end of the bag and tie it or otherwise maintain it in gathered condition about the base of the ear shoot. Any appropriate tie means (not shown), either separate or attached to the lower end of the bag, may be utilized.

FIG. 6 illustrates another embodiment of the bag of the present invention. FIG. 6 is similar to FIG. 2. The bag 1b of FIG. 6 differs from that of FIG. 2 only in that its side edges 5a and 6a are parallel, rather than tapering toward the lower end edge 8. The bag is otherwise the same as that of FIG. 2 and is closed and functions in the same manner. Therefore, like parts have been given like index numerals.

A preferred embodiment of the bag of the present invention is illustrated in FIGS. 7 through 10 wherein like parts are again given like index numerals. Turning first to FIG. 7, the bag blank is generally indicated at 35 and comprises a rectangular member having an upper edge 36, side edges 37 and 38, and a bottom edge 39. The blank is provided with a plurality of parallel, longitudinal fold lines 40 through 47. The blank may be of any appropriate material such as those described with respect to the embodiment of FIGS. 1 through 5.

The blank 35 makes up into the bag generally indicated at 48 in FIGS. 8 and 9. The bag 48 comprises a back panel 49 defined by the upper and lower edges 36 and 39 of the blank and fold lines 43 and 44. One side 50 of the bag is defined by the upper and lower edges 36 and 39 of the blank and fold lines 41 and 43. The side 50 is pleated by virtue of fold line 42, dividing the side 50 into pleat parts 50a and 50b.

The other side 51 of the bag is defined by the upper and lower edges 36 and 39 of the blank and fold lines 44 and 46. Again, the side 51 is provided with a fold line 45 rendering the side 51 pleated and defining pleat parts 51a and 51b.

The front panel of the bag is made up of two identical parts. The first front panel part 52 is defined by the upper and lower edges 36 and 39 of the blank and fold lines 40 and 41. The second front panel part 53 is defined by the upper and lower blank edges 36 and 39 and fold lines 46 and 47. Front panel part 52 is provided with a closure flap 54 defined by fold line 40, the blank side edge 37 and the upper and lower blank edges 36 and 39. Similarly, the front panel half 53 is provided with a closure flap 55 defined by the longitudinal edge of the blank, the upper and lower blank edges 36 and 39 and fold line 47.

The blank is folded to form bag 48 in the manner most clearly shown in FIGS. 8 and 9. It will be noted from FIG. 9 that the front panel made up of panel halves 52 and 53 is of greater width than the back panel 49. Furthermore, the pleat part 50b of bag side 50 is of greater width than pleat part 50a. Similarly, the pleat part 51b of bag side 51 is of greater width than pleat part 51a. The provision of a back panel 49 of lesser width than front panel 52-53 and pleated sides 50 and 51 tends to assure that the tubular bag will remain open for the passage of pollin from the corn plant tassel to the ear shoot during use, even when the bag is flexed by wind and movement of the corn plant.

This embodiment of the bag of the present invention is advantageous in that it is less expensive to manufacture and can more easily be applied to the corn plant. The manner of application to the corn plant is shown in FIG. 10 wherein a corn plant is generally indicated at 56, having a stalk 57, an ear shoot 58 and a tassel 69. As will be evident from FIGS. 7 through 9, the closure flaps 54 and 55 extend the full length of bag 48. The closure flaps 54 and 55 may be abutted and secured together in any appropriate manner. One easy and convenient way of attaching the closure flaps 54 and 55 together is to apply to their cooperating surfaces a waterproof, pressure sensitive adhesive of the type shown and described with respect to FIG. 2. Under these circumstances, it is only necessary to press closure flaps 54 and 55 together to close the bag 48. In applying the bag 48 to the corn plant 56, those portions of closure flaps 54 and 55 near the bottom end of the bag may be pressed together to form the lower end of the bag into a tubular structure. The lower end of the bag is then placed over the ear shoot 58. The lowermost end of the bag may thereafter be wrapped about the corn plant stalk 57 and joined together on the opposite side of stalk 57 from the ear shoot by any appropriate means such as staple 60 (FIG. 10). The procedure thus far described assures that the bag 48 will surround ear shoot 58 and will be firmly anchored to the corn plant at its lower end.

Thereafter, closure flaps 54 and 55 may be pressed together upwardly along bag 48 and about the base of tassel 59, as at 61. The closure flaps 54 and 55 may thereafter be joined together all the way to the upper edge of bag 48. At this point, bag 48 has been formed into a complete tubular structure surrounding both the ear shoot 58 and the tassel 59. The excess portion of the bag 48 at its uppermost end and above tassel 59 may then be folded upon itself and stapled or otherwise fastened together as at 62 to close the top of the bag. In accomplishing this last step, care should be taken to accommodate for further growth of the corn plant. As will be evident from FIG. 10, the bag 48 constitutes a tube connecting tassel 59 to ear shoot 58 and serving as a conduit for pollen from tassel 59 to the silk of ear should 58. Thus, bag 48 serves the same purpose as bag 1a of FIG. 5, or bag 1b of FIG. 6.

In accordance with the method of the present invention, any one of the bags 1a, 1b, or 48 is mounted on a corn plant in the manner described above before any of the ear shoot silk is exposed. The bag is caused to remain on the corn plant until harvest. Thus, the method contemplates the use of only a single bag and a single bagging step. The bag serves as a funnel so that the pollen produced by the corn plant tassel is concentrated on the silk of the ear shoot over a period of time. As a result, the earliest to the latest silk is pollinated producing a well filled ear. Thus, high inbred purity and high yield is assured. Exposure of the ear shoot silk to stray pollen is eliminated.

Although during the growing process the bag may be shaken from time to time to assure the descent of pollen therein, normal movement of the bag and plant by virtue of wind and the like will usually serve this purpose adequately. By virtue of its shape, any one of the bags of the present invention makes it easy to collect pollen at the bottom end of the bag without removing the bag from the corn plant, when in need of pollen for crossing with another plant. It would also be within the scope of the invention to locate the lowermost end of the bag about the ear shoot of an adjacent corn plant (not shown) for purposes of cross pollination.

Modifications may be made in the invention without departing from the spirit of it.

The embodiments of the invention in which an exclusive property or privilege is claimed are defined as follows:

1. A bag for use in the self-pollination of a corn plant having an ear shoot, a tassel and a tassel base portion, said bag comprising an elongated tubular member, said bag having a lower end portion configured to receive and surround the ear shoot of said corn plant, said bag having an upper end portion with means enabling said tassel base portion to extend from outside said upper end portion through and into said upper end portion and enabling said upper end portion to surround and enclose the tassel of said corn plant, the remainder of said bag being free of said corn plant and comprising a conduit connecting said upper portion enclosing said tassel and said lower portion surrounding said ear shoot whereby the pollen from said tassel is concentrated on the silk of said ear shoot to produce a well filled ear of excellent inbred purity and yield.

2. The structure claimed in claim 1, wherein said bag comprises an integral, one-piece structure of weatherproof, flexible material through which pollen from said tassel will not pass.

3. The structure claimed in claim 1 wherein said bag comprises a front panel and a rear panel, said means at said upper end of said bag enabling it to surround and enclose said tassel comprising a longitudinal slot in said front panel, said slot being of such length that said tassel may be received therethrough with the base portion of said tassel extending into said upper portion of said bag at the lowermost end of said slot, closure flap means configured to close all but said lowermost end of said slot through which said tassel base portion extends and closure flap means for the uppermost end of said bag above said tassel to close said uppermost end of said bag.

4. The structure claimed in claim 1, wherein said elongated tubular bag comprises a rear panel, pleated side panels and a pair of front panel halves provided with cooperating closure flaps extending the full length of said front panel halves and by which said front panel halves may be joined together to form said elongated tubular bag, said closure flaps at said upper end portion of said bag being closable about the base portion of said tassel so that said tassel may be received within and enclosed by said upper bag portion, the uppermost end of said bag being foldable upon itself above said tassel for the receipt of fastening means to maintain said uppermost bag end in folded condition to close said uppermost end of said bag.

5. The structure claimed in claim 3 wherein said bag is tapered toward said lower portion thereof.

6. The structure claimed in claim 3 including waterproof pressure-sensitive means in association with said closure flap means for said slot and said closure flap means for said uppermost end of said bag.

7. The structure claimed in claim 4 wherein said bag is formed from a rectangular blank of weatherproof, flexible material through which pollen from said tassel will not pass.

8. A process for the self-pollination of a corn plant having a tassel and an ear shoot comprising the steps of providing an elongated, flexible, tubular bag, enclosing said ear shoot in the lower portion of said bag and gathering the lower end of said bag about the base of said ear shoot before any of the ear shoot silk is exposed, enclosing said tassel in the upper end portion of said bag, closing the uppermost end of said bag above said tassel and maintaining said bag about said tassel and said ear shoot until harvest whereby said bag funnels substantially all of the pollen produced by said tassel to said ear shoot such that the earliest to the latest ear shoot silk are pollinated resulting in a well filled ear and excellent inbred purity.

9. The process claimed in claim 8, wherein said bag comprises an integral, one-piece structure of weatherproof, flexible material through which said pollen from said tassel will not pass.

10. The process claimed in claim 8 wherein said bag comprises a front panel and a rear panel with a longitudinal slot in said front panel extending from the uppermost end of said bag, closure flap means to close said slot and closure flap means to close the uppermost end of the bag, and including the steps of opening said slot and causing said tassel to pass therethrough into the interior of the uppermost end of said bag with the base of said tassel extending into said uppermost portion of said bag at the lowermost end of said slot, closing said slot from said tassel base to the uppermost end of said bag by means of said closure flap means for said slot and closing the uppermost end of said bag by means of said closure flap therefor.

11. The structure claimed in claim 8 wherein said elongated tubular bag comprises a rear panel, pleated side panels and a pair of front panel halves provided with cooperating closure flaps extending the full length of said front panel halves, said closure flaps having cooperating surfaces which may be abutted and maintained in abutted condition to close said flaps, join said front panel halves and from said elongated tubular bag, and including the steps of closing said closure flaps at the bottom portion of said bag and placing said bottom bags portion about said ear shoot, gathering the bottommost end of said bag about the base of said ear shoot and about the stalk of said corn plant, fastening said gathered bottommost bag portion together on the opposite side of said stalk from said ear shoot, closing said closure flaps up to and about the base of said tassel and thence to the uppermost end of said bag with said tassel located within the upper portion of said bag and folding the uppermost end of said bag upon itself above said tassel and fastening said folded uppermost bag end in its folded condition to close the upper end of said bag.

* * * * *